(12) United States Patent
Johnson et al.

(10) Patent No.: US 6,270,488 B1
(45) Date of Patent: Aug. 7, 2001

(54) LARGE VOLUME MEDICAL FLUID VACUUM COLLECTION CANISTER

(75) Inventors: Buster Johnson, Flint; Douglas Cundieff, Jacksonville, both of TX (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/490,980

(22) Filed: Jan. 24, 2000

(51) Int. Cl.$^7$ ........................................ A61B 19/00
(52) U.S. Cl. .............................................. 604/403
(58) Field of Search ........................... 604/903, 403, 604/118–121, 317, 319–323; 600/562, 573; 220/600, 610, 608, 604, 907, 908; 206/519, 520

(56) References Cited

U.S. PATENT DOCUMENTS

| | | |
|---|---|---|
| D. 285,658 | 9/1986 | Katz . |
| D. 307,393 | 4/1990 | Conrad . |
| 4,274,548 | 6/1981 | Schneider . |
| 4,579,260 | 4/1986 | Young et al. . |
| 4,609,106 | 9/1986 | Gentili . |
| 4,733,804 | 3/1988 | Slat et al. . |
| 4,744,785 | 5/1988 | Rosenthal et al. . |
| 4,781,314 | 11/1988 | Schoonover et al. . |
| 4,805,793 | 2/1989 | Brandt et al. . |
| 4,881,650 | 11/1989 | Bartz . |
| 4,923,098 | 5/1990 | Schoonover et al. . |
| 4,969,571 | 11/1990 | Bartz . |
| 4,969,922 | 11/1990 | Platte, Sr. . |
| 5,123,460 | 6/1992 | Reed . |
| 5,199,587 | 4/1993 | Ota et al. . |
| 5,199,588 | 4/1993 | Hayashi . |
| 5,299,710 | 4/1994 | Welsch et al. . |
| 5,598,941 | 2/1997 | Semersky et al. . |
| 5,792,126 | 8/1998 | Tribastone et al. . |
| 5,833,115 | 11/1998 | Eiten . |

*Primary Examiner*—Manuel Mendez
(74) *Attorney, Agent, or Firm*—Donald O. Nickey; John W. Cornell

(57) ABSTRACT

A large volume medical fluid vacuum collection canister includes a blow molded canister body defining a medical fluid receiving cavity. The canister body includes a pair of opposed upstanding sidewalls interconnected by a pair of opposed upstanding end walls a top wall with an opening and an opposed bottom wall. Each sidewall includes at least one reentrant beam portion extending inwardly from opposed sidewall surfaces into a central region of the medical fluid receiving cavity. The reentrant beams from opposing sidewalls are disposed in registering alignment so that there internal end faces abut in face to face relationship. The collection canister also includes a plurality of bellows recesses defined in the bottom wall and each of the opposed upstanding end walls. Each bellows recess extends the entire width of the bottom wall or end wall and further extends in a wrap around manner from the end wall or bottom wall portions to an intermediate point defined in the adjacent opposed sidewalls. The top opening of the collection canisters may be sealably connected to a vacuum system lid for use in a medical or surgical vacuum system. The canister bodies are specially configured and designed to provide an internal collection capacity of twelve liters or more and are designed to withstand internal vacuum pressures of up to 1.0 atmosphere of vacuum (or about 14.69 psi) without buckling or inwardly collapsing.

24 Claims, 5 Drawing Sheets

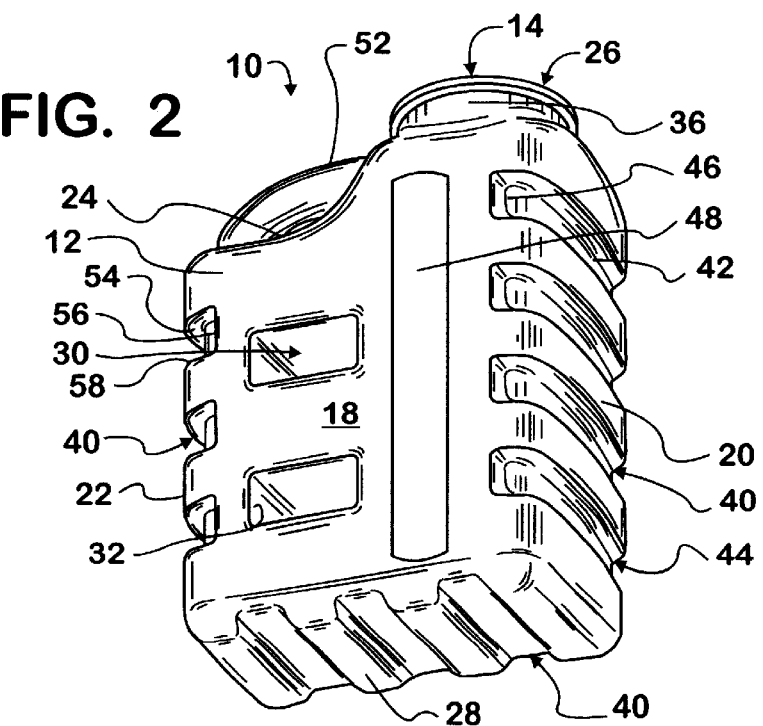
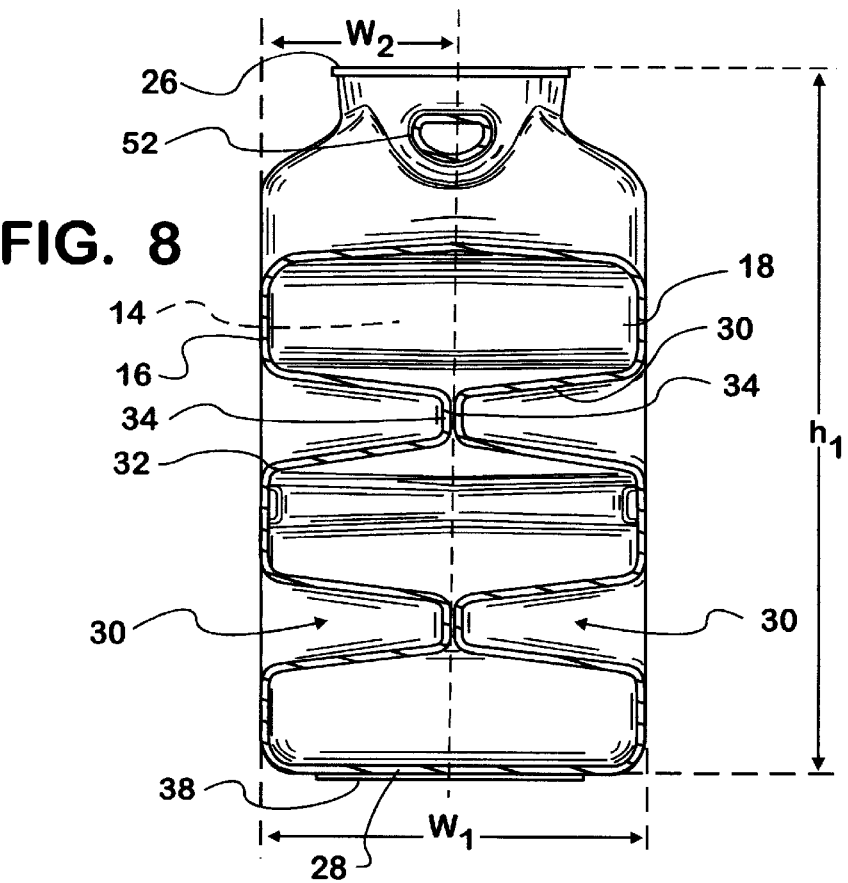

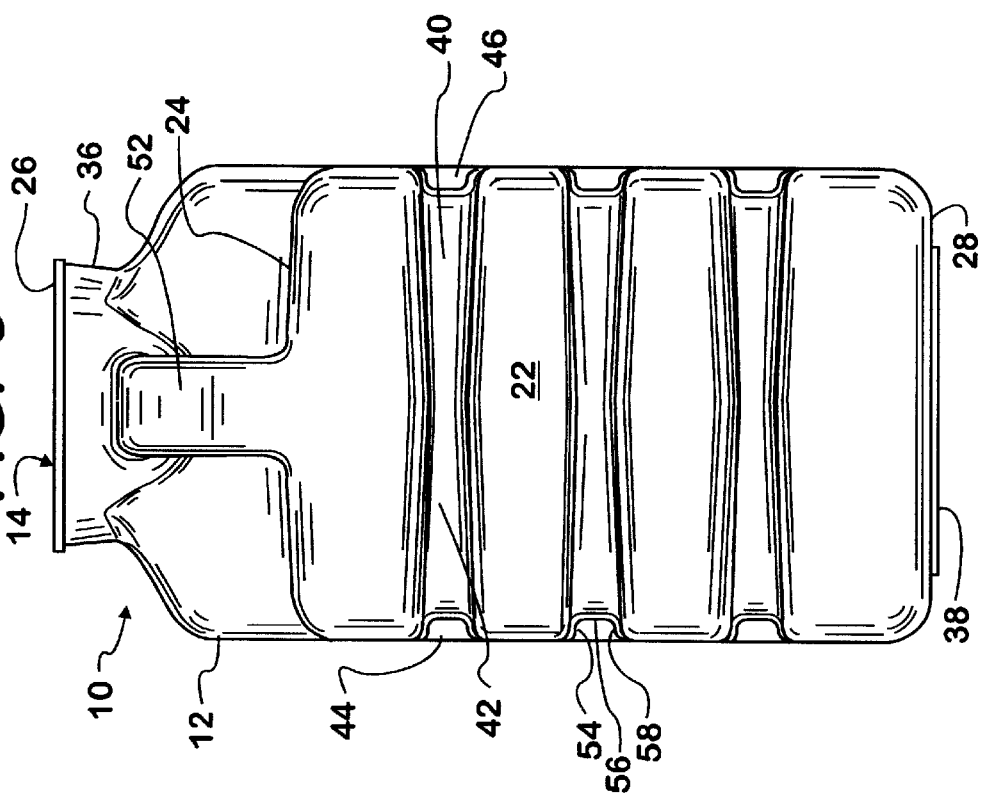
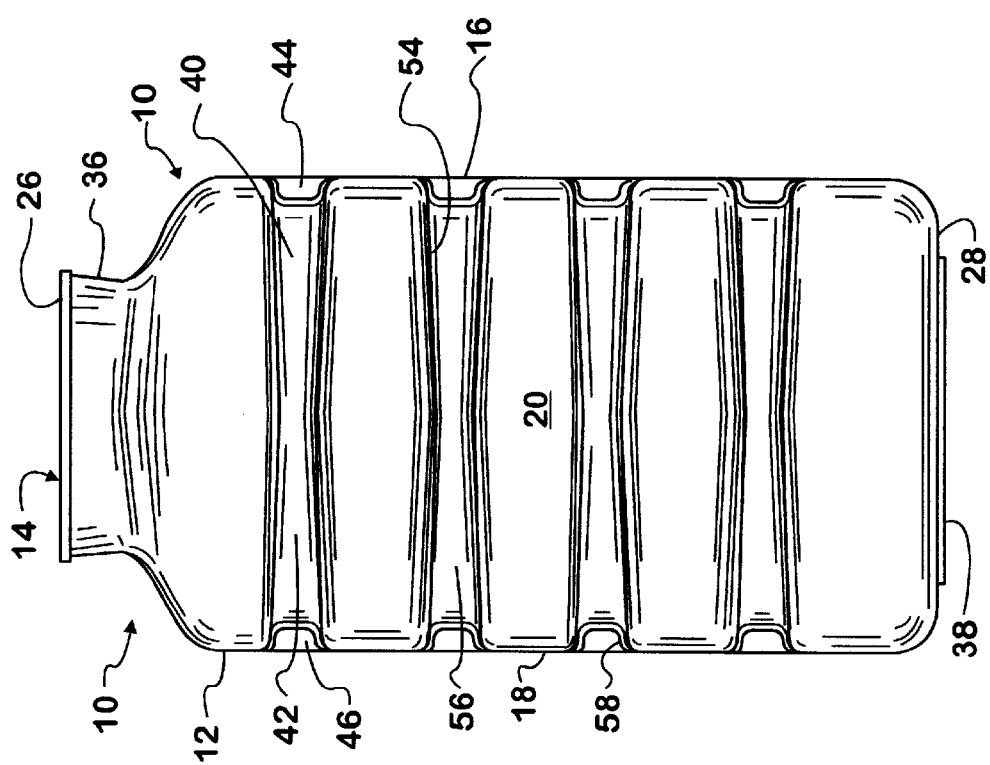

LARGE VOLUME MEDICAL FLUID VACUUM COLLECTION CANISTER

BACKGROUND OF THE INVENTION

The present invention relates to collection canisters designed for collecting, retaining and transporting medical fluids collected in surgical procedures. More particularly, the present invention relates to a new and improved blow molded fluid collection canister which, despite its thin wall thickness, can withstand internal vacuums of up to 1.0 atmosphere of vacuum (or about 14.69 psi) without buckling or inwardly collapsing.

Medical collection canisters have been used to collect and transport contaminated fluids generated in surgeries and other medical procedures. These prior art containers generally include open top buckets which collect fluids by gravity flow and vacuum canisters with portals which collect fluids from collection devices by applying a vacuum to one of the portals.

Open top buckets have been used to collect contaminated fluids from fluid collection devices in which the fluid flows from the collection devices to the bucket primarily due to the force of gravity. However, open top buckets pose serious health hazards because objects can fall into the bucket and splash the medical fluids on health care personnel. Open top buckets are difficult to transport and are susceptible to spilling. In addition, open top buckets are not sealed and are therefore unable to collect fluids by vacuum.

Prior art vacuum canisters have not been satisfactory, primarily because they have generally been too small for use in all medical procedures. Prior art vacuum canisters typically contain between 800 and 3,000 cubic centimeters of fluid. Many surgical procedures use large quantities of irrigation fluids, such as orthoscopic and cystoscopic surgery. These types of surgery have been known to utilize an amount of irrigation fluid significantly in excess of 3,000 cc. Furthermore, many extended surgical procedures such as liposuction, organ harvesting, organ transplantation, and open heart surgery produce significantly more than 3,000 cc of contaminated body fluids. Accordingly, numerous prior art vacuum canisters were required in many surgical procedures. These canisters are painstakingly connected in series and/or demand an extensive amount of attention by healthcare personnel. This creates the need for additional healthcare personnel in the operating room or divides the attention of existing healthcare personnel. Surgical procedures may be frequently interrupted to change the vacuum canisters. These interruptions may extend the length of the procedure which is decidedly disadvantageous to the patient.

Because of these shortcomings, collection systems capable of collecting larger volumes of fluid are required which do not involve the need for tandem setups, e.g. the hook up of several similar smaller containers to one vacuum source and one suction tubing end piece. Moreover, more cost effective manufacturing for large canisters is required. The only currently available large volume collection canisters capable of collecting volumes significantly larger than three liters are injection molded and have thick walls to prevent the canister from collapsing during use. The surface area of these prior art injection molded bucket canisters is relatively large and, the force which is directly proportional to the surface area, will increase significantly on the outside of the canister when a vacuum or negative pressure is pulled on the inside of the canister. The thick walled designs have an undesirably high material cost for their manufacture.

At present, the desire for high performance, low cost, large volume collection canisters for use with vacuum collection systems in medical procedures remains unsatisfied.

SUMMARY OF THE INVENTION

In order to remedy the shortcomings and deficiencies of the prior art devices, the present invention provides, in an embodiment, a new and improved large volume medical fluid vacuum collection canister for collecting medical fluids in surgical procedures. The collection canister preferably comprises a blow molded canister body defining a medical fluid receiving cavity. The canister body includes a pair of opposed upstanding sidewalls interconnected by a pair of opposed upstanding end walls, a top wall with an opening and an opposed bottom wall. The canister body has a generally rectangular cross-sectional configuration.

Each sidewall includes at least one re-entrant beam portion extending inwardly from a recess opening disposed in a central region of the sidewall to a beam end face disposed adjacent a middle of the medical fluid receiving cavity. The re-entrant beam portions extending inwardly from opposing sidewalls are disposed in registering alignment with each other so that their respective end faces are disposed in abutting face to face relationship. Preferably, the abutting end faces are connected together, such as by fusing in the molding process.

The bottom wall and each of the opposed end walls includes at least one inwardly directed bellows recess. Each bellows recess includes a central portion extending an entire width of the bottom wall or the end wall and includes a pair of opposed wrap around end portions extending from the central portion around the container an intermediate point defined in an adjacent sidewall. The top opening maybe sealably connected to a vacuum system lid for use in a medical or surgical vacuum system. The canister body is specially configured and designed to withstand internal vacuum pressures in the medical fluid receiving cavity of up to about 1.0 atmosphere of vacuum (or about 14.69 psi) of vacuum without buckling or inwardly collapsing.

In an embodiment, the upstanding end walls and bottom wall each include a plurality of bellows recesses.

In an embodiment, the re-entrant beam portions have a generally tapered four sided configuration which taper inwardly from the recess opening to the beam end face so that the beam end face has a smaller surface area than the surface area defined by the recess opening in the sidewall.

In an embodiment, all corner edges provided by intersecting surfaces of the container are all gently radiused to avoid any sharp edges. Each bellows recess has a generally three sided rectangular cross-section with radiused corner portions.

In an embodiment, the collection canister may further comprise a handle portion disposed above the top wall. In an embodiment, an elongate vertically oriented transparent or translucent viewing window may be provided in an upstanding side wall or both of the upstanding sidewalls to permit fluid filling height of medical fluids collected within the medical fluid receiving cavity to be visually observed from the outside of the container.* (Clear label —transparent or translucent polymer.)

In an embodiment, the collection canister is dimensioned and configured to define a medical fluid collection cavity of at least three liters and preferably up to about 9 to about 12 liters or more.

In an embodiment, the new and improved collection canisters are blow molded from a thermoplastic polymer molding composition. The thermoplastic polymer may comprise a variety of homopolymer, copolymer or polymer blend materials. These polymer formulations may include impact modifiers, fillers, dissimilar polymers and many other additives which are conventionally added to improve the processing properties or final physical properties of the canister. Preferably, the canister body comprises a thermoplastic polymer material having a Young's modulus of from about 200,000 psi to about 500,000 psi. Alternatively, the collection canister is preferably blow molded from a transparent or translucent material so that fluid fill height may be viewed directly through an upstanding sidewall. A see through label having volumetric markings may be placed on the sidewall to permit easy collected volume readings, or volumetric markings may be molded-in the sidewall during blow molding of the canister. A preferred canister comprises a thermoplastic polycarbonate material comprising only polycarbonate or comprising a blend of polycarbonate with a second thermoplastic molding resin. An especially preferred canister comprises a transparent or translucent blow moldable grade of a thermoplastic polyolefin molding composition such as polystyrene, polypropylene and clarified polypropylene.

The new and improved collection canisters having a nominal wall thickness of about 0.125 inch are able to withstand loading pressures of about 1.0 atmosphere of vacuum (or about 14.69 psi) without exhibiting inward collapse or buckling. In fact, the new and improved collection canisters are able to withstand maximum stresses of up to 5,000 psi or more and exhibit a maximum displacement of only 0.65 inch at these greatly elevated vacuum pressures and stresses. The unique combination of structural features permit extremely satisfactory large volume medical fluid vacuum collection canisters to be blow molded with significant material savings. Moreover, the new and improved large volume blow molded collection canister is structurally able to withstand significant pressure loading with a much thinner sidewall thickness as compared with prior art vacuum collection canisters.

Other objects and advantages provided by the present invention will become apparent from the following Detailed Description taken in conjunction with the Drawings in which:

BRIEF DESCRIPTION OF THE DRAWINGS

FIG. 2 is a perspective view of the new and improved collection canister of the present invention showing the underside or bottom wall of the collection canister;

FIG. 4 is an elevated front view of the new and improved collection canister;

FIG. 5 is an elevated rear end view of the collection canister;

FIG. 8 is an elevated cross-sectional view of the new and improved collection canister taken along view lines 8—8 in FIG. 3.

DETAILED DESCRIPTION OF THE PREFERRED EMBODIMENT

Figure 1:
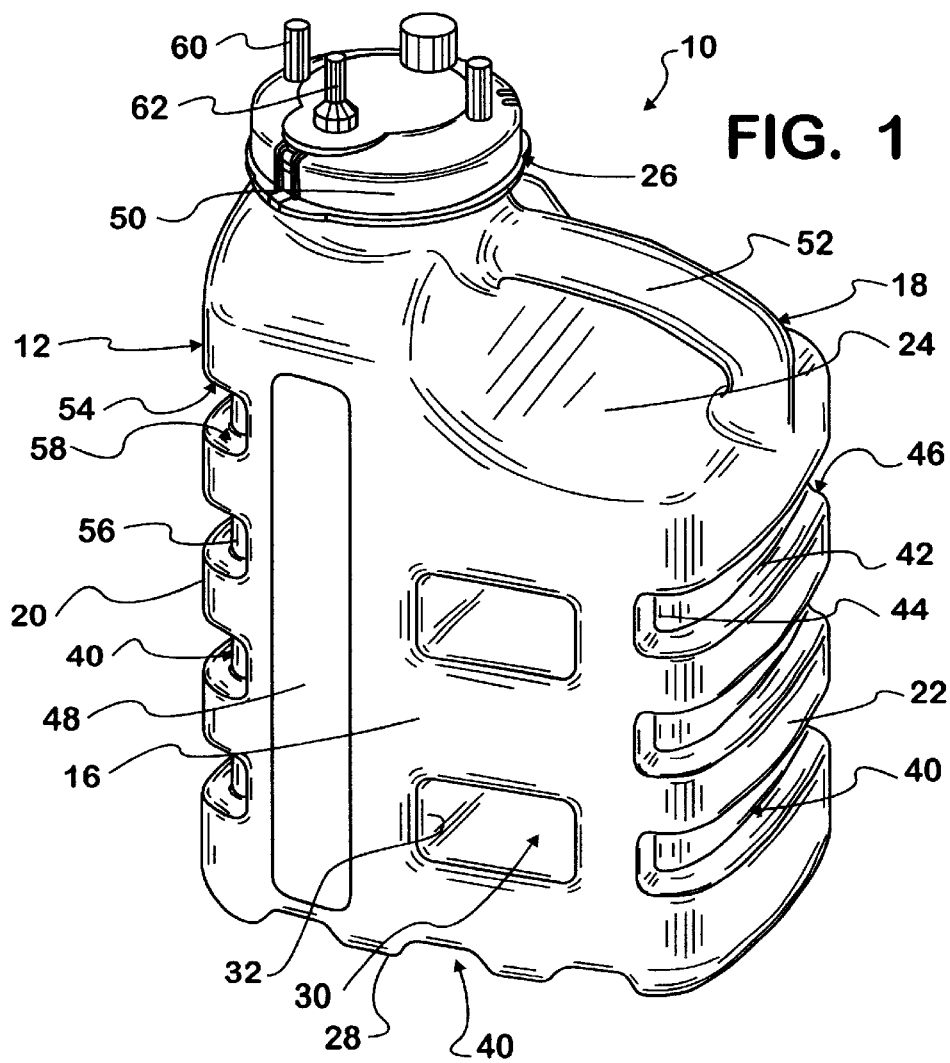
FIG. 1 is a perspective view of the new and improved large volume collection canister of the present invention shown with its top opening closed with a sealed vacuum lid for use in suction collection of medical fluids during a surgical procedure.
Figure 6:
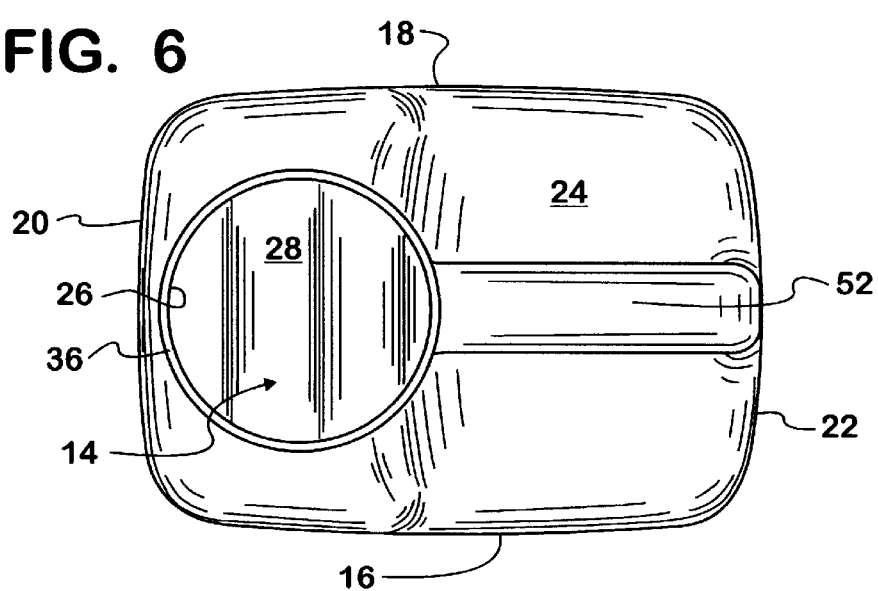
FIG. 6 is a top plan view of the new and improved collection canister.

Referring now to FIGS. 1–8, a new and improved medical fluid collection canister, in accordance with an embodiment of the present invention, is designated generally by reference numeral 10. As shown in the Drawings, collection canister 10 is configured to provide a large volume medical fluid vacuum collection canister for collecting medical fluids in surgical procedures. Generally, fluid collection canister 10 is a waste collection canister designed for use in any surgical procedure which uses large amounts of irrigation fluid or which produces large amounts of contaminated fluid. The canister may be used to collect fluid from floor pedal aspirators, orthoscopic shavers, fluid collecting drapes and other fluid collecting devices which can be used for cystoscopic surgery, orthoscopic surgery, or any surgical procedure which uses a large quantity of irrigation fluid. Canister 10 may be used in extended surgical procedures which result in large amounts of contaminated body fluids such as liposuction, organ harvesting, organ transplantation and open heart surgery, or in any other medical application.

Figure 3:
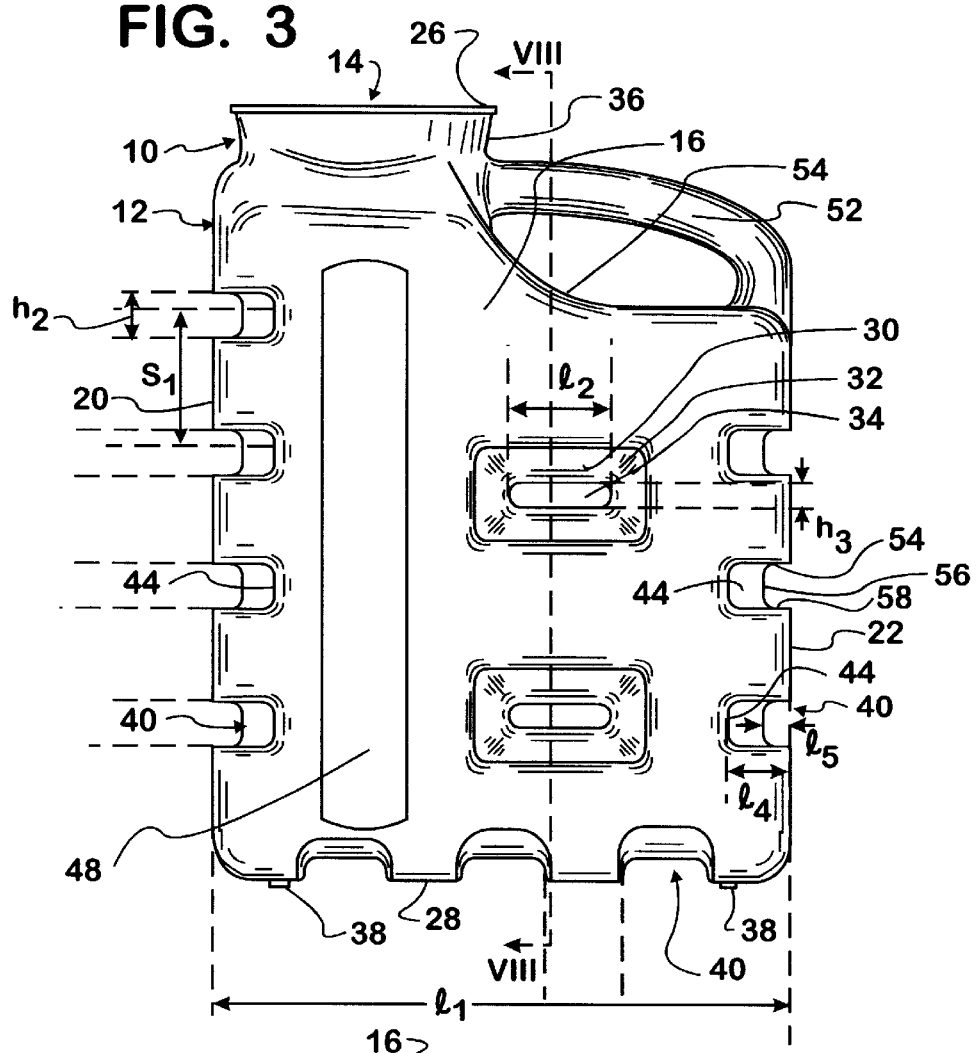
FIG. 3 is an elevated side view of the new and improved collection canister of the preferred embodiment.

The new and improved large volume medical fluid vacuum collection canister 10 preferably comprises a unitary or one piece blow molded canister body 12 which defines a medical fluid receiving cavity 14. Canister body 12 includes a pair of opposed upstanding sidewalls, such as left wall 16 and right wall 18, interconnected by a pair of opposed upstanding end walls, such as front wall 20 and rear wall 22. A top wall 24 with an opening 26 interconnects the upstanding side and end walls and an opposed bottom wall 28 also connects the lower end portions of the upstanding side and end walls. Canister body 12 has a generally upstanding rectangular cross-sectional configuration and includes a height dimension, $h_1$, as shown in FIG. 8, defined between the top opening 26 and bottom wall 28. Canister body 12 includes a length dimension, $l_1$, defined between the front and rear walls as shown in FIG. 3. Canister body 12 further includes a width dimension, $w_1$, defined between the left sidewall 16 and right sidewall 18 as shown in FIG. 8. Canister body 12 is specially configured to be able to withstand vacuum pressures of up to about 1.0 atmosphere of internal vacuum (or about 14.69 psi) without any of the sidewalls or endwalls or bottom wall or top wall buckling or collapsing in an inward manner.

In accordance with the preferred embodiment depicted in FIGS. 1–8, canister body 12 includes at least one reentrant beam portion 30 defined in each of sidewalls 16 and 18 respectively which extend inwardly from a recess opening 32 disposed in a central region of sidewall 16 or 18. The reentrant beam portions 30 extend inwardly from the sidewall surface to a beam end face 34 which is disposed at about a central axis of container body 12, such that the beam end faces 34 are positioned at about a middle section of the medical fluid receiving cavity 14. In the preferred embodiment depicted in FIGS. 1–8, sidewall 16 and sidewall 18 each include a pair of spaced apart reentrant beam portions 30. As is best shown in FIG. 8, the reentrant beam portions 30 extending inwardly from opposed sidewalls 16 and 18 are preferably disposed in registering alignment with their respective end faces 34 disposed in abutting, face to face relationship. The reentrant beam portions are provided to prevent inward collapse of the container sidewalls 16 and 18 on application of internal vacuum pressures and also serve to prevent inward collapse of front wall 20 and rear wall 22.

Bottom wall 28 and the opposed front and rear walls 20 and 22 respectively each include at least one inwardly directed bellows recess 40. In the preferred embodiment depicted in FIGS. 1–8, a plurality of inwardly directed bellows recesses 40 are defined in front wall 20 and rear wall 22. Each bellows recess 40 includes a horizontally extending central portion 42 which extends the entire width of bottom wall 28 or a respective end wall 20 and 22. Wrap around end portions 44 extend from each central portion 42 into left sidewall 16 and wrap around end portions 46 extend from central portion 42 to an intermediate point defined in adjacent right sidewall 18. As shown, all of the connecting surface portions found within container 10 including within the reentrant beam portion 30 and the inwardly directed bellows recesses 40, are each provided with radiused intersecting corners, throughout the entire container.

As shown in FIG. 1, the new and improved collection canister 10 is adapted to sealably receive a vacuum cap or lid 50 which may be sealably mounted on top opening 26 about upstanding peripheral lip 36 in order to aspirate fluids and collect them in the medical fluid receiving cavity 14. The vacuum cap 50 is of the type well known to those skilled in the art and, as shown, includes four upstanding portals for connection to various tubing elements, including upstanding portal 60, which may be collected by tubing to any fluid collection device. Specimen traps, in the form of a sock or sleeve, may be placed on the inside of these ports for collecting and separating solid specimens from remaining fluids in a well known manner. Vacuum port 62 is provided for making a tubing connection to a source of vacuum, either house vacuum or vacuum pump. The remaining unnumbered ports may be provided for making additional tubing connections as may be desired in accordance with arrangements well known to those skilled in this art.

In accordance with the preferred embodiment depicted in FIGS. 1–8, each recess opening 32 of each reentrant beam portion 30 and each beam end face 34 are each provided with a generally four sided configuration with radiused corners. Each reentrant beam portion 30 tapers inwardly from its recess opening 32 to its respective beam end face 34. In a preferred embodiment, the abutting beam end faces 34 of aligned and opposing reentrant beam portions 30, one from left sidewall 16 and one from right sidewall 18 are, connected to each other, preferably by being fused together during the blow molding process. Thermal welding, ultrasonic welding or adhesive bonding might also be employed to secure the beam end faces together. Although two spaced apart reentrant beam portions 30 are disposed in left sidewall 16 and right sidewall 18 as shown, one larger reentrant beam portion might be substituted as shown in the alternate embodiment of FIG. 9, or more than two reentrant beam portions may also be used.

As shown in FIGS. 1–3, in accordance with the preferred embodiment, canister body 12 is blow molded from a see-through transparent or translucent polymer material. The fill height of collected medical fluids collected in cavity 14 can be visually observed from the outside of container 10. A see-through label 34 can be secured to sidewalls 16 and 18 as shown which includes volumetric markings, so that collected fluid volumes may be quantitatively read. Alternatively, a transparent or translucent viewing window may be provided in place of label 34 to permit inspection of the fluid fill level within container body 12 from the outside. A volumetric scale may also be provided along viewing window 48 to permit a reading of collected volumes to be readily made.

In addition, in the preferred embodiment shown in the Drawings, container body 12 is provided with a handle portion 52 disposed above a top wall 24 to provide ease of carrying and lifting. Other configurations for a handle such as 52 will be readily apparent to those skilled in this art and may be used herein.

In accordance with the preferred embodiment shown in FIGS. 1–8, front wall 20, rear wall 22 and bottom wall 28 are each provided with a plurality of bellows recesses 40. Each bellows recess 40 has a generally three sided rectangular cross-section with radiused corners. Accordingly, each bellows portion 40 defines a downwardly facing shoulder surface 54, an indented vertical indent surface 56 and an upwardly facing shoulder surface 58. As shown in FIG. 3, the vertical indent surface 56 of each bellows portion 40 is preferably varied as shown in FIGS. 4–5 so that the value of $h_2$ is relatively smaller adjacent the center midline of front wall 20 and rear wall 22 and gradually becomes larger as the height $h_2$ is measured approaching corner portions. The wrap around continuations 44 and 46 of the bellows recesses 40 further contribute to the collapse resistance of the container body under vacuum.

Moreover, the relative spacing and placement of the bellows recesses 40 and the reentrant beam portions 30 is selected so that they cooperate together to minimize development localized stresses to prevent any inward buckling or collapse of the sidewalls, front wall, rear wall, bottom wall or top wall.

As shown in the preferred embodiment depicted in FIGS. 1–8, the number of bellows recesses 40 provided in the front wall 20 may be the same or different from the number provided in the rear wall 22. The bellows recesses 40 provided in the front wall 20 may be disposed in alignment with the bellows recesses 40 in the rear wall 22 or they may not be so aligned.

Figure 7:
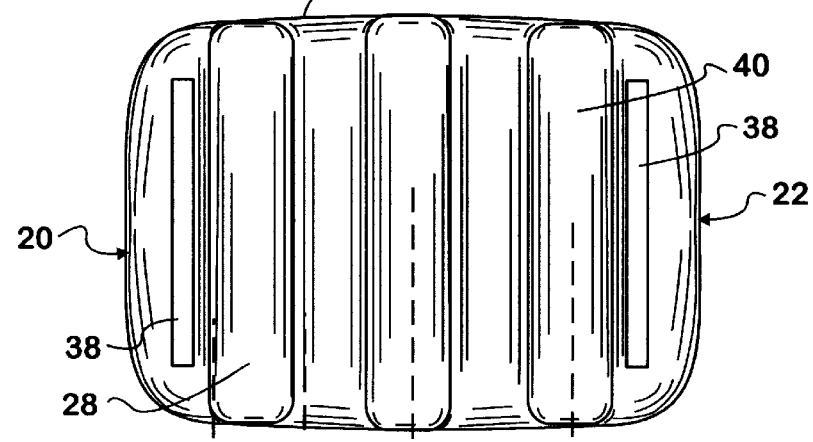
FIG. 7 is a bottom plan view of the new and improved collection canister.

As shown in FIGS. 3 and 7, in the preferred embodiment, canister body 12 includes a plurality of regularly spaced bellows recesses 40 extending along a middle section of front wall 20 and a middle section of rear wall 22. The maximum height dimension $h_2$ of each bellows recess 40 is preferably about ¼ to about ½ of a center line spacing, S1, of adjacent bellows recesses 40 in the same end wall, either front wall 20 or rear wall 22. Bottom wall 28 includes a plurality of regularly spaced bellows recesses 40 as well. The regularly spaced bellows recesses 40 extend along a midsection of bottom wall 28.

As shown in FIG. 7, each bellows recess 40 in bottom wall 28 preferably has a length dimension $l_3$ which is approximately equal to about 0.25 to 0.75 times the center line spacing $s_2$ between adjacent bellows recesses 40 and bottom wall 28 as shown.

As shown in FIG. 3, in accordance with the preferred embodiment depicted therein, each beam end face 34 has a length dimension, $l_2$, which is from about ⅛ to about ½ of the length dimension, $l_1$, of the container body 12 defined between front wall 20 and rear wall 22. Also as shown in FIG. 3, in accordance with the preferred embodiment, each bellows recess 40 in front wall 20 and rear wall 22 has a recess depth shown as dimension, $l_5$. Each wrap around end portion 44 or 46 extends inwardly from the edge of upstanding sidewall 16 or 18 by a dimension, $l_4$, as shown. In accordance with the preferred embodiment, dimension $l_4$ is at least about two times $l_5$. Although the preferred embodiment includes bellows recesses having particular depth configuration and center line spacing, variations in the preferred dimensions for each of these features may be made by those skilled in the art and still maintain the antibuckling characteristics required for canister body 12 in use. These dimensional ratios are merely preferred and are provided to further illustrate a preferred embodiment of the present invention.

Figure 9:
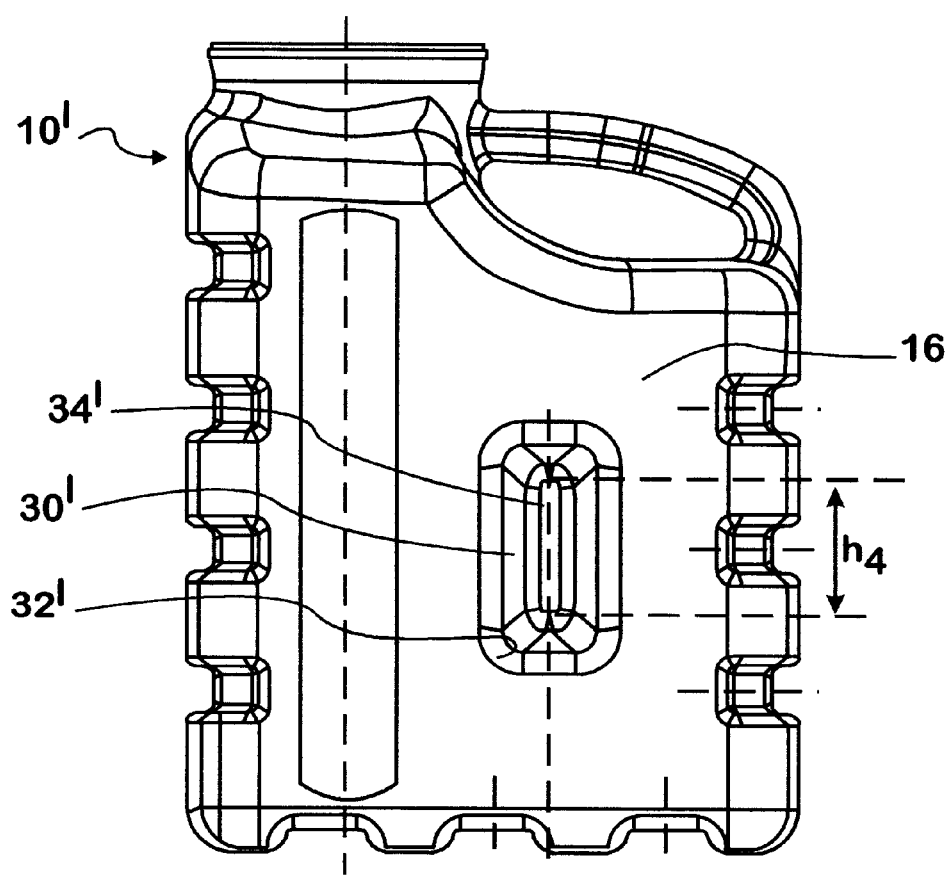
FIG. 9 is an elevated side view of an alternate embodiment of the new and improved collection canister in accordance with the present invention.

Referring to the alternate embodiment of the collection canister $10^1$ shown in FIG. 9, instead of two pairs of reentrant beam portions 30 being provided in each sidewall 16 and 18, collection canister $10^1$ is provided with a single reentrant portion $30^1$ in sidewalls $16^1$ and $18^1$. the long dimension of beam end face $34^1$ indicated as, $h_4$, is oriented so that it extends parallel to height dimension, $h_1$. Preferably, $h_4$ is from about 0.2 to about 0.5 times $h_1$.

Collection canister 10 is designed and configured so that medical fluid receiving cavity 14 has a volume of greater than about three liters. Preferably, medical fluid receiving cavity 14 has a volume of at least about 9 to about 12 liters or more.

Canister body 12 comprises a blow molded thermoplastic polymer. Preferably, the canister body comprises a thermoplastic polymer material having a Young's modulus of from about 200,000 psi to about 500,000 psi. A preferred thermoplastic polymer for blow molding to form canister body 14 is a transparent or translucent thermoplastic polyolefin or thermoplastic polycarbonate material. Homopolymers, copolymers and polymer blends may be used. Blow moldable grades of polyolefins, such as polystyrene, polypropylene and clarified polypropylene are preferred as well as polycarbonate materials. The thermoplastic molding composition may include other resins blended to the polyolefin or polycarbonate to improve final properties as well as any conventional additives known to those skilled in this art. For example, the thermoplastic molding composition may include impact modifiers, antistatic agents, mold release agents, agents added to improve crazing and cracking resistance, flame retardant agents and the like without limitation. Suitable blow moldable thermoplastic polyolefin and polycarbonate compositions are available commercially from a number of sources. Polycarbonate and Teflon® blends or other polymers or blend compositions may also be used, provided the final container body, when shaped in accordance with the configuration taught by the present invention, provides the necessary buckling resistance to internal vacuum loading.

In accordance with the preferred embodiment, the blow molded canister body 12 is blow molded to have a nominal wall thickness of about 0.125 inch. New and improved canister 10 and $10^1$ configured as shown in FIGS. 1–9 and having a nominal wall thickness of about 0.125 inch on testing were able to withstand loading pressures of 1.0 atmosphere of vacuum (or about 14.69 psi) without exhibiting any inward collapse or buckling. In fact, when studied in finite element analysis testing, these new and improved collection canisters were able to withstand maximum stresses of up to 5,000 psi or more and exhibit only a maximum displacement of 0.65 inch at these greatly elevated vacuum pressures.

The new and improved large volume medical fluid vacuum collection canisters are blow molded and provided with a unique combination of cooperating structural features. The new and improved large volume medical fluid vacuum collection canisters in accordance with the present invention provide improved large volume collection canisters exhibiting excellent vacuum resistant performance as compared with prior art vacuum collection canisters, while providing significant material savings.

Although the present invention has been described with reference to certain preferred embodiments, modification or changes may be made therein by those skilled in this art without departing from the scope and spirit of the present invention as defined by the appended claims.

We claim:

1. A large volume medical fluid vacuum collection canister for collecting medical fluids in surgical procedures comprising:

a blow molded canister body defining a medical fluid receiving cavity, the canister body including a pair of opposed upstanding sidewalls inter-connected by a pair of opposed upstanding end walls, a top wall with an opening and an opposed bottom wall, the canister body having a generally rectangular cross-sectional configuration, each sidewall including at least one re-entrant beam portion extending inwardly from a recess opening disposed in a central region of the sidewall to a beam end face disposed adjacent a middle of the medical fluid receiving cavity, the re-entrant beam portions of the opposing sidewalls being disposed in registering alignment with their respective end faces disposed in abutting face to face relationship, the bottom wall and each of the opposed end walls each including at least one inwardly directed bellows recess, each bellows recess including a central portion extending an entire width of said bottom wall or end wall and a pair of opposed wrap around end portions extending from the central portion to an intermediate point defined in the adjacent sidewall, the top opening being sealably connectable to a vacuum system lid and the canister body being constructed to withstand vacuums of up to about 1.0 atmosphere without buckling or inwardly collapsing.

2. A collection canister as defined in claim 1, wherein the upstanding end walls and the bottom wall each include a plurality of bellows recesses, respectively.

3. A collection canister as defined in claim 1, wherein the upstanding sidewalls each include a plurality of re-entrant beam portions.

4. A collection canister as defined in claim 1, wherein each recess opening and beam end face have a generally four-sided configuration and the re-entrant beam portion tapers inwardly from the recess opening to its respective beam end face.

5. A collection canister as defined in claim 1, further comprising a handle portion disposed above the top wall.

6. A collection canister as defined in claim 1, wherein each said bellows recess has a generally 3-sided rectangular cross section with radiused corners.

7. A collection canister as defined in claim 1, wherein said canister body has a height dimension defined between the top opening and the bottom wall, a length dimension defined between the opposed end walls which is less than or equal to the height dimension and a width dimension defined between the opposed sidewalls which is less than the length dimension.

8. A collection canister as defined in claim 1, wherein abutting beam end faces of aligned and opposing re-entrant beam portions are connected to each other.

9. A collection canister as defined in claim 1, further comprising an elongate viewing window extending parallel to a height dimension of the canister body defined in at least one of the upstanding sidewalls permitting filling height of medical fluids within the medical fluid receiving cavity to be observed.

10. A collection canister as defined in claim 1, wherein the canister body is blow molded and has a nominal wall thickness of about 0.125 inches.

11. A collection canister as defined in claim 1, wherein the canister body is configured so that the medical fluid receiving cavity has a volume of greater than three liters.

12. A collection canister as defined in claim 1, wherein the canister body is configured so that the medical fluid receiving cavity has a volume of about 9 liters to about 12 liters, or more.

13. A collection canister as defined in claim 1, wherein the canister body comprises a blow molded transparent or translucent thermoplastic polymer.

14. A collection canister as defined in claim 1, wherein the canister body comprises a thermoplastic polycarbonate material or a thermoplastic polyolefin material.

15. A collection canister as defined in claim 1, wherein the canister body comprises a thermoplastic polymer material having a Young's modulus of from about 200,000 psi to about 500,000 psi.

16. A collection canister as defined in claim 1, wherein the opposed end walls include a plurality of bellows recesses, respectively, and the number of the bellows recesses in the opposed end walls is not the same.

17. A collection canister as defined in claim 1, wherein the top opening in the top wall is bounded by a raised peripheral lip and has a generally circular cross-sectional configuration.

18. A collection canister as defined in claim 16, wherein some of the bellows recesses in the opposed end walls are disposed in an aligned position at the same height.

19. A collection canister as defined in claim 1, wherein the opposed end walls include a plurality of regularly spaced bellows recesses extending along a midsection of the end wall.

20. A collection canister as defined in claim 1, wherein the opposed end walls include a plurality of regularly spaced bellows recesses extending along a midsection of the end wall and a height dimension of each bellows recess is about one third a centerline spacing of adjacent bellows recesses in the end wall.

21. A collection canister as defined in claim 1, wherein each beam end face has a length dimension which is from about $1/8$ to about $1/2$ of a length dimension of the container body defined between the opposed end walls.

22. A collection canister as defined in claim 1, wherein the bottom wall includes a plurality of regularly spaced bellows recesses.

23. A collection canister as defined in claim 1, wherein the bottom wall includes a plurality of regularly spaced bellows recesses extending along a midsection of a length of the bottom wall.

24. A collection canister as defined in claim 23, wherein each bellows recess in the bottom wall has a length dimension approximately equal to about 0.25 to about 0.75 times a centerline spacing between adjacent bellows recesses in the bottom wall.

* * * * *